US007195179B2

(12) United States Patent
Miller et al.

(10) Patent No.: US 7,195,179 B2
(45) Date of Patent: Mar. 27, 2007

(54) PIEZOELECTRIC MIST GENERATION DEVICE

(75) Inventors: Craig Miller, State College, PA (US); Andreas Hadjicostis, Carmel, IN (US)

(73) Assignee: Piezo Technologies, Indianapolis, IN (US)

( * ) Notice: Subject to any disclaimer, the term of this patent is extended or adjusted under 35 U.S.C. 154(b) by 224 days.

(21) Appl. No.: 10/858,489

(22) Filed: Jun. 1, 2004

(65) Prior Publication Data

US 2005/0035216 A1 Feb. 17, 2005

Related U.S. Application Data

(60) Provisional application No. 60/475,144, filed on Jun. 1, 2003.

(51) Int. Cl.

| | |
|---|---|
| ***A62C 13/62*** | (2006.01) |
| ***B05B 1/08*** | (2006.01) |
| ***B05B 1/26*** | (2006.01) |
| ***B05B 17/04*** | (2006.01) |
| ***A61M 11/06*** | (2006.01) |

(52) U.S. Cl. ................ 239/302; 239/102.1; 239/102.2; 239/338; 239/461; 239/1; 239/4; 239/11

(58) Field of Classification Search ................ 239/302, 239/102.1, 102.2, 338, 461, 1, 4, 11
See application file for complete search history.

(56) References Cited

U.S. PATENT DOCUMENTS 4,031,171 A 6/1977 Asao et al.
4,582,654 A 4/1986 Karnicky et al.
5,217,165 A 6/1993 Takahashi et al.
5,299,739 A 4/1994 Takahashi et al.
6,338,809 B1 1/2002 Hampden-Smith et al.
6,422,684 B1 7/2002 Ladabaum et al.
6,540,153 B1 * 4/2003 Ivri .............................. 239/4

(Continued)

FOREIGN PATENT DOCUMENTS

WO WO-94/08727 4/1994

OTHER PUBLICATIONS

Adiga, K.C. et al., "Self-Entraining Ultrafine Water Mist Technology for New Generation Fire Protection." NanoMist Systems, LLC, Warner Robins, GA, 2003.

(Continued)

*Primary Examiner*—Davis Hwu
(74) *Attorney, Agent, or Firm*—Woodard, Emhardt, Moriarty McNett & Henry LLP

(57) ABSTRACT

An apparatus of the present invention includes: a container operable to hold a liquid; circuitry operable to provide an electrical stimulus; and a piezoelectric element electrically coupled to the circuitry. The piezoelectric element includes a first face positioned beneath the liquid when the liquid is placed in the container, the piezoelectric element being responsive to the electrical stimulus to produce acoustic energy that causes droplets to form from the liquid. The piezoelectric element has a focal length along a focal axis intersecting the first face. The piezoelectric element and the container are structured in relation to one another to form an oblique angle between the focal axis and an axis generally parallel to a surface of the liquid when the liquid is at rest in the container.

35 Claims, 6 Drawing Sheets

U.S. PATENT DOCUMENTS

| | | | | |
|---|---|---|---|---|
| 6,629,646 | B1 * | 10/2003 | Ivri | 239/4 |
| 6,799,729 | B1 * | 10/2004 | Voic | 239/102.2 |
| 2002/0006470 | A1 | 1/2002 | Eberspacher et al. | |
| 2003/0051886 | A1 | 3/2003 | Adiga et al. | |

OTHER PUBLICATIONS

Jenkins, D.R., "Free Surface Shape for an Ultrasonic Nebuliser." CSIRO Mathematical and Information Sciences, Australia, Date unknown.

Yang, Jiann C., et al., "Fire Suppression Efficiency Screening Using a Counterflow Cylindrical Burner." Proceedings of the 5th ASME/JSME Joint Thermal Engineering Conference, San Diego, CA, Mar. 1999.

Yang, Jiann C., et al., "Recent Results from the Dispersed Liquid Agent Fire Suppressant Screen." Halon Options Technical Working Conference, Albuquerque, NM, Apr. 1999, pp. 95-104.

"Ultrasonically Induced Fountains and Fogs," *NASA Tech Briefs*, Sep. 2002.

* cited by examiner

PIEZOELECTRIC MIST GENERATION DEVICE

CROSS-REFERENCE TO RELATED APPLICATIONS

The present application claims the benefit of U.S. Provisional Patent Application No. 60/475,144 filed 1 Jun. 2003, which is hereby incorporated by reference in its entirety herein.

INTRODUCTION

The present invention relates to droplet generation, and more particularly, but not exclusively, relates to the generation of ultrafine mists with a piezoelectric device for fire suppression, humidification, medical treatment, sterilization, coating application, pesticide/herbicide application, and/or particle preparation, to name just a few.

One embodiment of the present invention is a unique droplet generation technique. Other embodiments include unique methods, systems, devices, and apparatus for generating droplets with ultrasonic energy and/or one or more piezoelectric devices.

A further embodiment of the present application includes a container holding a liquid, circuitry operable to provide an electrical stimulus, and a piezoelectric element electrically coupled to the circuitry. The piezoelectric element is positioned beneath the liquid and is responsive to the electrical stimulus to produce acoustic energy that causes droplets to form from the liquid. The piezoelectric element and the container are structured in relation to one another to form an acute angle between a focal axis for the element and a segment of an axis generally parallel to a surface of the liquid when the liquid is at rest in the container. In one form, at least some of the droplets have a diameter of one micrometer or less. Alternatively or additionally, the element is one of several each arranged with respective focal axes that intersect in a region within the container.

Yet a further embodiment includes a container holding a liquid and several piezoelectric elements coupled to the container. The piezoelectric elements each respond to a corresponding electrical stimulus to produce acoustic energy with a focal length along one of a corresponding number of focal axes. These elements are positioned relative to one another to cause at least some of the focal axes to intersect within the container and to be covered by the liquid when placed in the container to an operable level. Circuitry is also included that is coupled to the piezoelectric elements. The circuitry provides the corresponding electrical stimulus to each of the piezoelectric elements. In one form, a conduit is provided that is in fluid communication with the container, and the acoustic energy of each of the elements is directed through the liquid to form droplets that the conduit directs to a desired location. Alternatively or additionally, the piezoelectric elements are spatially oriented in an arrangement corresponding to a concave surface.

Another embodiment includes a container to hold a liquid, several piezoelectric elements coupled to the container, and circuitry coupled to the piezoelectric elements. The piezoelectric elements and the container are structured to cover the piezoelectric elements with the liquid when held in the container at an operable level. The piezoelectric elements each respond to a corresponding oscillatory electrical stimulus from the circuitry to produce acoustic energy that causes formation of a mist from a portion of the liquid held in the container. A preferred form includes at least 20 piezoelectric elements, a more preferred form includes at least 50 piezoelectric elements, and an even more preferred form includes at least 100 piezoelectric elements. For forms directed to ultrafine mist production, it is preferred the mist include droplets with a diameter of one micrometer or less, more preferred that at least 20% of the mist by droplet quantity is comprised of droplets with a diameter of one micrometer or less, even more preferred that at least 50% of the mist by droplet quantity is comprised of droplets with a diameter of one micrometer or less, and most preferred that the mist have a mean droplet diameter of one micrometer or less.

Still another embodiment of the present application includes: providing a container coupled to several piezoelectric elements; determining a desired liquid level for the container as a function of one or more focal lengths of the piezoelectric elements; placing a liquid in the container to the desired liquid level to cover the piezoelectric elements; activating the piezoelectric elements each with an electrical stimulus provided at a frequency of at least eight megahertz to direct acoustic energy through the liquid; and forming a mist from a portion of the liquid in response to the acoustic energy. A preferred form includes at least 20 piezoelectric elements, a more preferred form includes at least 50 piezoelectric elements, and an even more preferred form includes at least 100 piezoelectric elements. For forms directed to ultrafine mist production, it is preferred the mist include droplets with a diameter of one micrometer or less, more preferred that at least 20% of the mist by droplet quantity is comprised of droplets with a diameter of one micrometer or less, even more preferred that at least 50% of the mist by droplet quantity is comprised of droplets with a diameter of one micrometer or less, and most preferred that the mist have a mean droplet diameter of one micrometer or less.

A further embodiment includes: providing a container coupled to a piezoelectric element; placing a liquid in the container to a selected level to cover the piezoelectric element; and activating the piezoelectric element with an electrical stimulus to direct acoustic energy through the liquid along a focal axis. The focal axis forms an acute angle with an axis parallel to the selected level and a mist is formed from a portion of the liquid in response to the acoustic energy.

These and further embodiments, objects, features, aspects, benefits, advantages, and forms of the present invention shall become more apparent from the detailed description and figures provided herewith.

DETAILED DESCRIPTION OF SELECTED EMBODIMENTS

Figure 1:
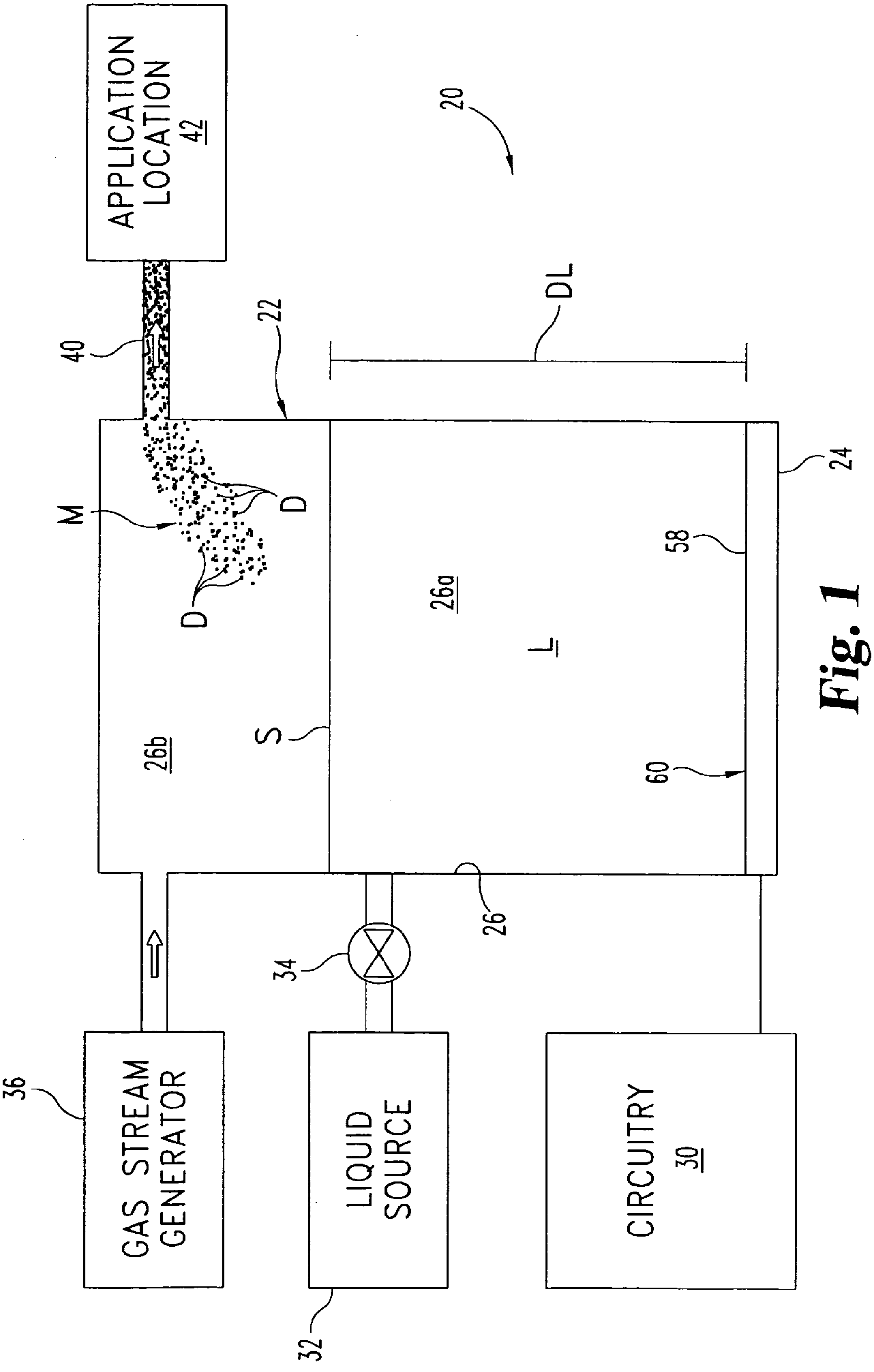
FIG. 1 is a schematic view of a first droplet generation system.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

One embodiment of the present invention includes a unique technique to generate a high volume of mist for fire suppression, humidification, medical treatment, sterilization, coating application, pesticide/herbicide application, particle preparation, and the like. A unique device directed to mist production includes one or more piezoelectric elements operated in an ultrasonic frequency range to form the mist from a liquid covering the elements. In one arrangement, acoustic energy generated by the elements is focused relative to a desired liquid level in a container and the ultrasonic frequency is controlled to generate a mist composed of droplets with a desired size.

FIG. 1 depicts droplet generation system 20 of another embodiment of the present invention. System 20 includes container 22 with base 24. Container 22 has a hollow interior chamber 26 arranged to hold liquid L in reservoir portion 26*a*. Chamber 26 also includes a head space 26*b* above liquid L that typically includes a gas, such as air, nitrogen, or the like. System 20 further includes circuitry 30 electrically coupled to base 24, liquid source 32 coupled to controllable valve 34, gas stream generator 36 in fluid communication with head space 26*b*, and conduit 40. Valve 34 selectively regulates the flow of liquid from source 32 into chamber 26. Generator 36 can be a fan or other source of pressurized gas to create a gas flow through head space 26*b* and conduit 40. Conduit 40 is in fluid communication with head space 26*b* and application location 42. Container 22 and conduit 40 are illustrated in a schematic sectional manner to facilitate understanding of certain internal features of system 20.

Figure 2:
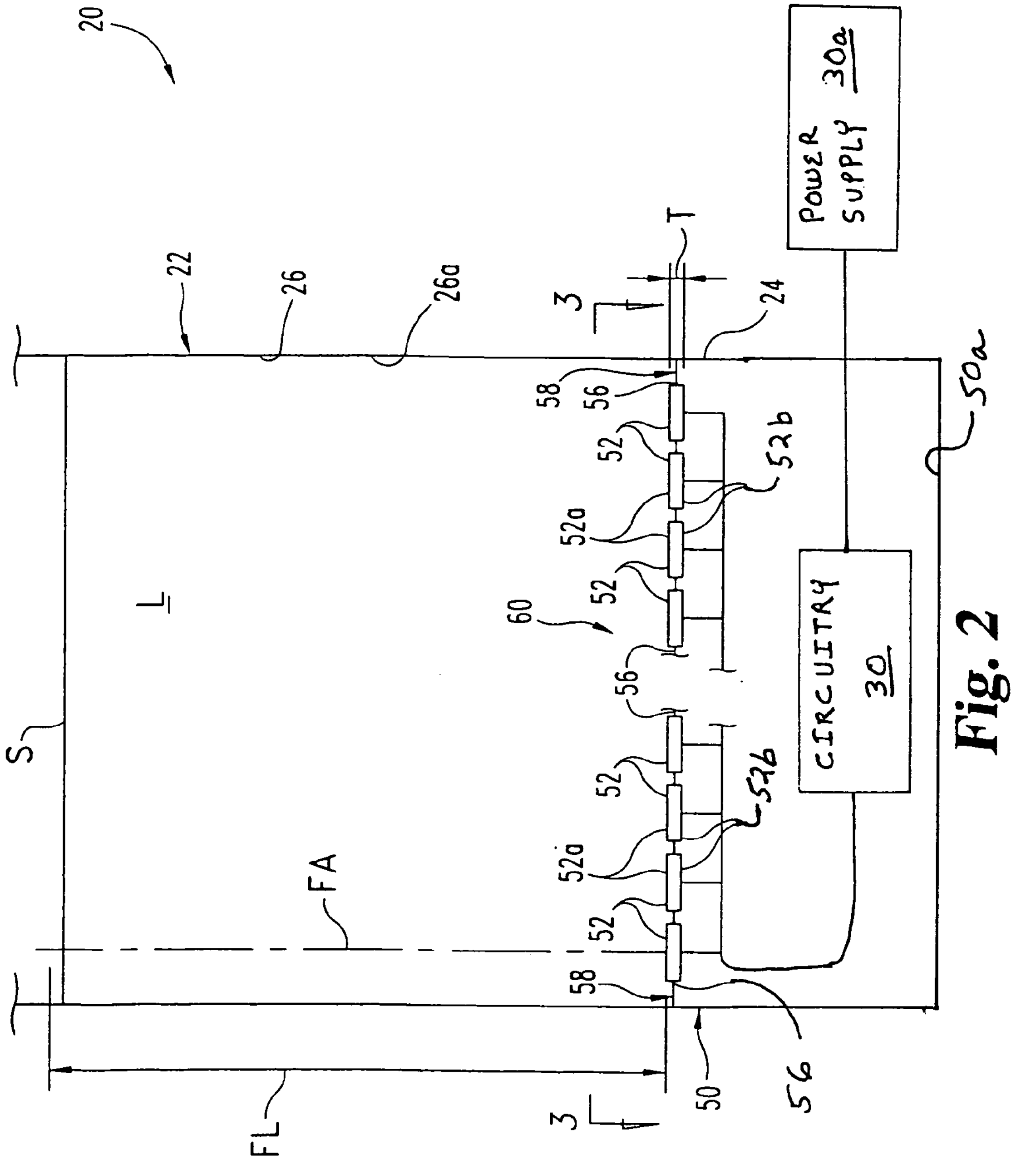
FIG. 2 is a partial, schematic side view of a portion of the FIG. 1 system shown in greater detail.
Figure 3:
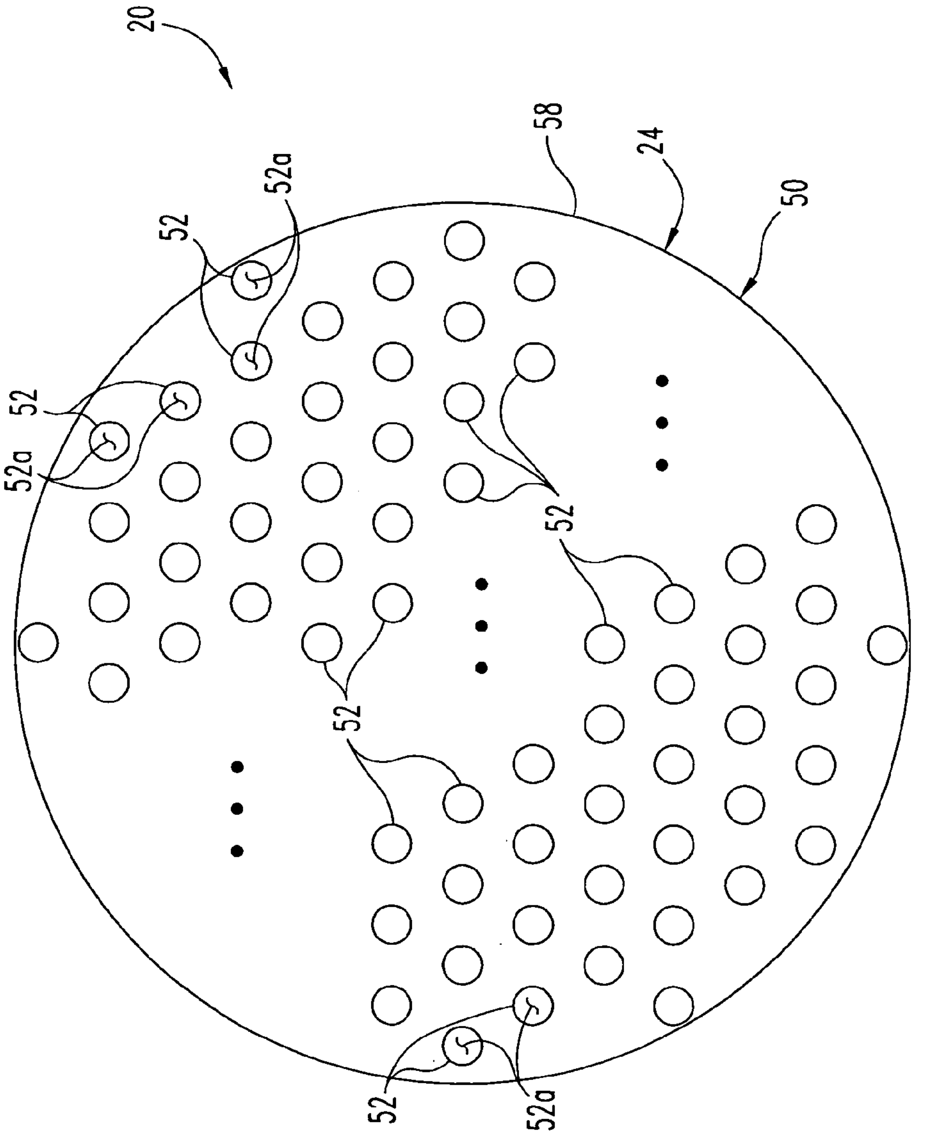
FIG. 3 is a schematic sectional view of a portion of the FIG. 1 system taken along section line 3—3 of FIG. 2.

Referring additionally to FIGS. 2 and 3, further details of system 20 are shown. Base 24 includes ultrasonic transducer assembly 50. In FIG. 2, container 22 and base 24 are shown in a schematic sectional manner to facilitate understanding of certain internal features of system 20. FIG. 3 is a schematic sectional view corresponding to section line 3—3 of FIG. 2. Assembly 50 is comprised of a number of piezoelectric elements 52, cabling 54, mounting seals 56, and apertured floor member 58. Alternatively, assembly 50 is designated multielement transducer 60.

Elements 52 each include a pair of electrodes (not shown) electrically coupled to circuitry 30 by cabling 54 in a standard manner. Cabling 54 can be comprised of individually insulated wires, coaxial cables, or such different arrangement as would occur to those skilled in the art for the particular application. Each element 52 is positioned relative to a corresponding aperture of floor member 58 and mounted thereto. A corresponding one of mounting seals 56 is used in mounting each of elements 52 to floor member 58 to prevent leakage of liquid L into assembly space 50*a*.

Each element 52 has face 52*a* opposite face 52*b*. Face 52*a* is oriented upward to be in contact with liquid L and face 52*b* is oriented downward to be in contact with air in assembly space 50*a*. Each element 52 is of a ceramic material with an approximately planar, circular disk shape as best shown in the partial top view of FIG. 3. Alternatively or additionally, element 52 can be shaped with a differently shaped curvilinear perimeter (including but not limited to an elliptical or oval type, just to name a couple of examples), a differently shaped rectilinear perimeter (including but not limited to a rectangular, hexagonal, triangular, or other polygonal type, only to name a few examples), a combination of curvilinear and rectilinear features, and/or may have a curved face to correspondingly provide a different focus. In one particular form, a concave face provides advantageous focusing characteristics with an operating frequency at or above 5 megahertz (MHz).

In response to an appropriate electrical stimulus, each element 52 is polarized to ultrasonically vibrate primarily in the direction of its thickness, as represented by segment T. This configuration tends to generate compressional waves in liquid L. Correspondingly, each element 52 has one electrode on face 52*a* and the other electrode on face 52*b*. For each element 52, the first electrode on face 52*a* can extend to face 52*b* for electrical connection purposes, wrapping around the element edge. In one particular form, this first electrode forms a ring-shaped contact pad on face 52*b*, and the second electrode is in the form of a disc-shaped contact pad concentrically located within this ring-shaped pad and spaced apart therefrom by an electrically insulating circular gap. Typically, the first electrode would be designated as electrical ground for such an arrangement. As shown in FIG. 3, elements 52 are positioned along floor member 58 in a generally uniform pattern, each being generally equally spaced apart from one another. In FIG. 3 not all elements are shown to preserve clarity—instead being represented by ellipses. Moreover, only a few of elements 52, faces 52*a*, faces 52*b*, and seals 56 are designated by reference numerals in FIGS. 2 and 3 to preserve clarity.

Circuitry 30 is configured to provide an oscillatory electrical stimulus to each of the elements 52 via cabling 54. Circuitry 30 is provided in assembly space 50*a* of assembly 50, and in one particular form is provided as a number of multiple-component, printed circuit board subassemblies mounted generally parallel to one another. For this particular form, each such subassembly may provide the driving circuitry for a designated element 52 or multiple element subset. Circuitry 30 is powered with power supply 30*a*, which while operatively coupled to circuitry 30, is shown outside assembly space 50*a* in FIG. 2. Naturally, in other embodiments, circuitry 30 and/or power supply 30*a* can be arranged differently.

In response to the oscillatory electrical stimulus from circuitry 30, element 52 generates acoustic power sufficient to form droplets D from liquid L that collectively comprise mist M schematically shown in FIG. 1. The quantity and size of droplets D depends on the frequency and power level of the electrical stimulus provided with circuitry 30. Typically, circuitry 30 includes a separate driver circuit for each element 52, although a driver circuit to power more than one element 52 at a time can alternatively be used. It should be appreciated that while circuitry 30 (absent power supply 30*a*) is included in assembly space 50*a*, in other embodiments, at least a portion, if not all of circuitry 39 can be positioned external to assembly space 50*a*—such that it is not housed in assembly 50.

Figure 6:
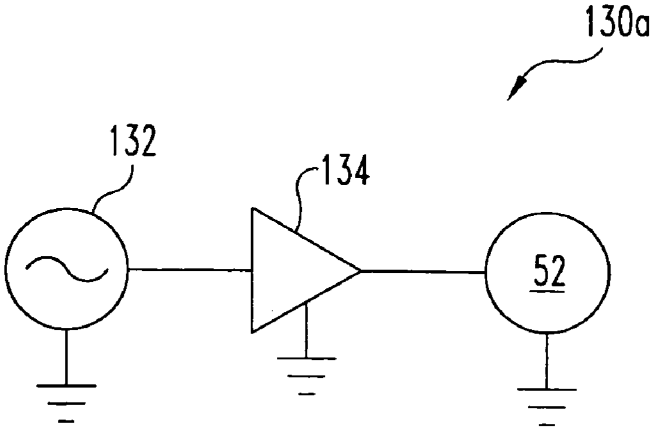
FIG. 6 is a schematic view of a first type of piezoelectric driver circuit that can be included in the circuitry for any of the systems of FIGS. 1–5.
Figure 7:
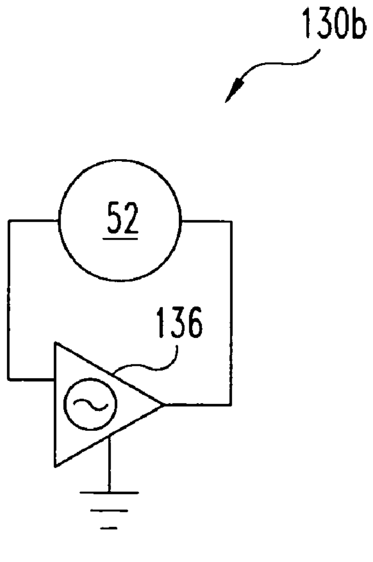
FIG. 7 is a schematic view of a second type of piezoelectric driver circuit that can be included in the circuitry for any of the systems of FIGS. 1–5.

Referring to FIGS. 6 and 7, alternative forms of driver circuits 130*a* and 130*b* are illustrated. Circuit 130*a* of FIG.

6 includes an oscillator 132 that generates a signal at the desired ultrasonic frequency. Oscillator 132 can be any of several standard circuit types, with its frequency being fixed or variable over a desired range. Generally, the output from oscillator 132 is not sufficient to vibrate element 52 at a desired power level. Accordingly, the signal output from oscillator 132 is provided to power amplifier 134. Amplifier 134 is operable to both increase the power level and provide an electrical impedance match to improve the efficiency of power transfer from amplifier 134 to element 52. Power amplifier 134 provides a desired level of gain to correspondingly generate the desired acoustic energy output of the corresponding element 52.

Circuit 130*b* of FIG. 7 includes an oscillator and amplifier combined into power oscillation circuit 136 with element 52 in a feedback loop to control frequency—such that element 52 is included in the oscillator circuitry. Typically, circuit 130*b* more readily tunes to the resonant frequency of element 52, self-regulating resonant frequency drift due to aging, temperature and the like. In contrast, circuit 130*a* may need to include compensation circuitry (not shown) to account for changes in resonant frequency of element 52, depending on desired performance. On the other hand, circuit 130*a* can typically generate more acoustic power per element 52 than can circuit 130*b*. Electrical power can be provided to circuitry 30 from one or more batteries, the standard power grid, and/or a different source as would occur to those skilled in the art. Typically, input electrical power is converted to a form suitable for the components of circuitry 30 with a standard type of power supply (not shown) as appropriate.

Generator 36 is provided to assist with directing the flow of mist M from head space 26*b* through conduit 40 to location 42. Circuitry 30, source 32, valve 34, and/or generator 36 can be coupled to an operator control station and/or automatic control station suitable for the desired application of system 20. In one form, such stations include one or more processors configured to control and regulate various operations of system 20. For a fire suppression application, one or more sensors or detectors are coupled to the station to determine is mist M should be produced in response to a condition indicating a fire at location 42. Alternatively or additionally, conduit 40 can include one or more valves to direct or limit the flow of mist M to location 42. In still other embodiments, one or more of source 32, valve 34, generator 36, and/or conduit 40 may be absent.

For each piezoelectric element, the ultrasonic energy beam generated in response to the electrical stimulus from circuitry 30 is directed towards surface S of liquid L (see FIGS. 1 and 2). The ultrasound beam from a piezoelectric source has a natural focal point at the transition point of the near field distance ($N_o$), where the intensity of the ultrasound reaches a maximum. This transition point distance is related to element size and frequency of operation by: $N_o = d^2 f/4c$ where d is the diameter of element 52, f is the operating frequency and c is the speed of sound in liquid L. A corresponding relationship can be determined using standard techniques for a noncircular element shape. It has been discovered that the rate of mist production is maximized when the surface of the liquid L is at or just before the near field distance. The near field distance is alternatively designated the "focal length" herein. Referring to FIG. 2, focal length FL of the leftmost element 52 is illustrated along a corresponding focal axis FA. The desired or selected level DL of liquid L in container 22 is also illustrated in FIG. 1 and can be determined as a function of focal length FL of one or more of elements 52.

The desired size of droplets D forming mist M is determined primarily by the frequency of operation for a given element 52. The mean size of droplets D is:

$$d_n = 0.34(8\pi s/\rho f^2)^{\frac{1}{3}};$$

where: s is the liquid surface tension, p is the liquid density, and f is the frequency of oscillation. For applications in which liquid L is water and mist M is being provided for fire suppression, units have been operated at frequencies ranging from 0.5 MHz to 12 MHz corresponding to mean droplet sizes of approximately 7 μm to 0.9 μm (micrometer). For applications directed to ultrafine mist production (at least some of which are directed to fire suppression), it is preferred the mist include droplets with a diameter of one micrometer or less, more preferred that at least 20% of the mist by droplet quantity is comprised of droplets with a diameter of one micrometer or less, even more preferred that at least 50% of the mist by droplet quantity is comprised of droplets with a diameter of one micrometer or less, and most preferred that the mist have a mean droplet diameter of one micrometer or less. However, in other embodiments, the droplet size and/or operating frequency can vary.

It has been discovered that the rate of mist production corresponds to the power level of the ultrasound. Depending on the application, power levels of less than one watt to hundreds of watts may be desired. The collective power level depends not only on the acoustic energy level generated with a given element 52, but also the number of elements 52. For fire suppression with mist M, a preferred form includes at least 20 piezoelectric elements 52, a more preferred form includes at least 50 piezoelectric elements 52, and an even more preferred form includes at least 100 piezoelectric elements 52.

The thickness T of each piezoelectric element can be determined relative to its composition and desired frequency of element operation. Accordingly, thickness T can relate to the droplet size generated. Alternatively or additionally, the number, size, shape, orientation, and/or composition of elements 52 can vary, which can influence the rate of droplet/mist production. For multiple element embodiments, they can be arranged is many different patterns which depend at least on the shape of the container, the chamber, and the number of elements. Moreover, in other embodiments, one or more elements 52 can be sized, shaped, oriented, and/or composed differently relative to one or more other of elements 52. In one alternative embodiment, only a single piezoelectric element is present.

The intensity of the ultrasound beam may be increased by focussing it with a concave curvature of the piezoelectric element surface. This focussing approach moves the point of maximum intensity closer to the element and reduces the range of liquid depths over which the intensity is great enough to produce useable amounts of mist compared to a generally flat form. In one particular arrangement, one or more of elements 52 are of a type with a concave surface along face 52*a* to provide a relatively short focal length relative to a planar variety.

Figure 4:
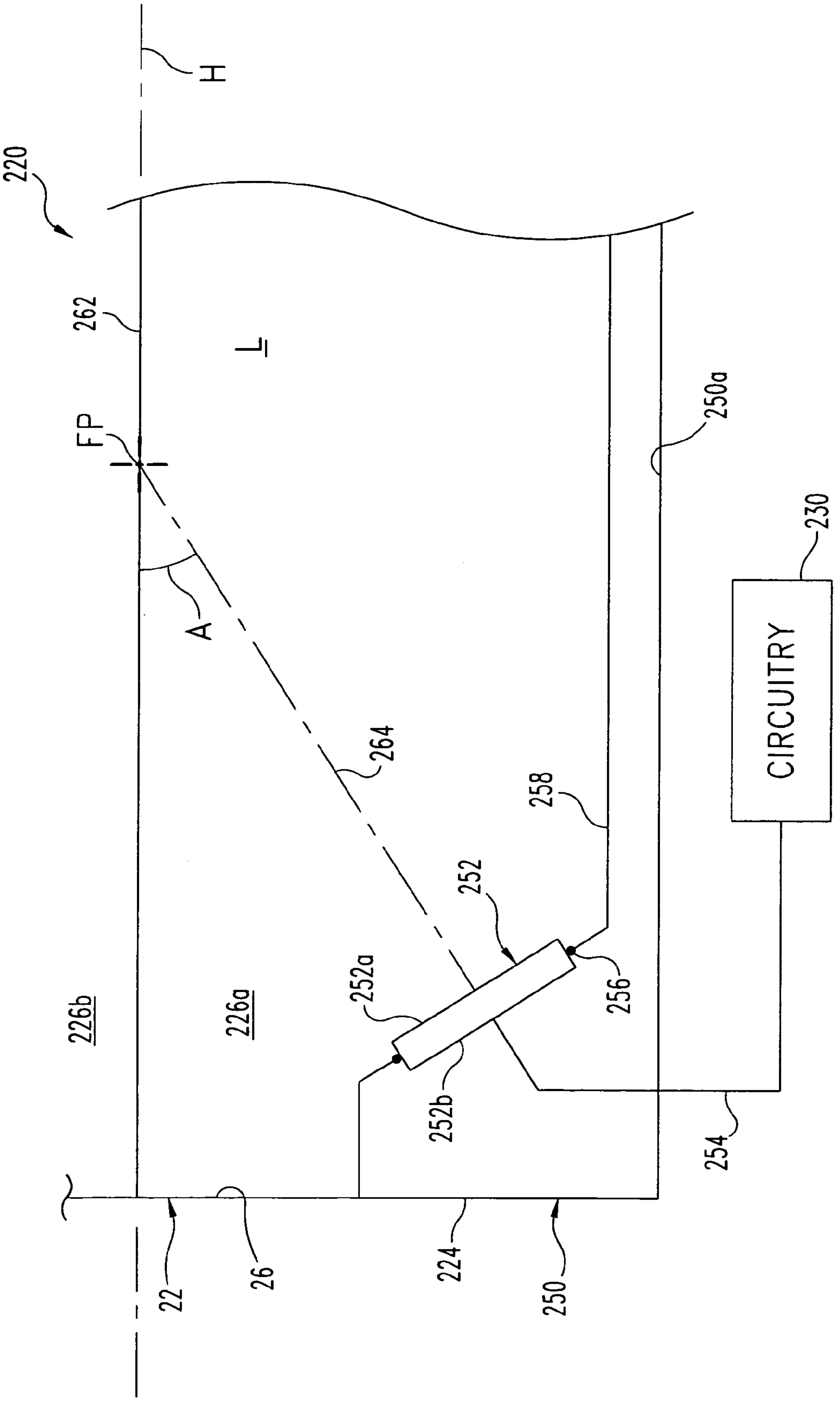
FIG. 4 is a partial, schematic view of a second droplet generation system.

As an alternative to the structure of assembly 50, one or more of elements 52 can be in a separate housing placed on the bottom of chamber 26 and/or fixed to side walls of the container at various angular positions. Indeed, it has been found that the angle at which the ultrasound beam intersects the liquid surface can be varied to enhance the mist production, which is believed to follow from the resulting increase in atomizing surface area. For example, as a circular element is tilted, its atomizing surface changes from a circular area to an elliptical area that is greater than the corresponding circular area—depending on frequency of operation and focus character. Referring to FIG. 4, droplet generation system 220 is illustrated, where like reference numerals refer to like features. System 220 includes container 22 with base 224. Container 22 defines hollow interior chamber 26 holding liquid L in reservoir portion 226*a*. Head space 226*b* is provided above liquid L. Container 22 can be coupled to source 32 via valve 34, generator 36, and/or conduit 40 in the manner previously described in connection with FIG. 1 (not shown). Container 22 and base 224 are again schematically illustrated in section to show certain internal features.

Base 224 includes transducer assembly 250. Assembly 250 includes a substantially flat piezoelectric element 252 with face 252*a* in contact with liquid L and opposing face 252*b* in contact with air in assembly space 250*a*. Element 252 is mounted in relation to an aperture through floor member 258 with mounting seal 256 to prevent leakage of liquid L into space 250*a*. Element 252 is electrically coupled to circuitry 230 by cable 254 in a standard manner. Circuitry 230 includes a driver circuit for element 252 of the circuit 130*a* type shown in FIG. 6, the circuit 130*b* type shown in FIG. 7, or such different type as would occur to those skilled in the art. Some or all of circuitry 230 can reside in space 250*a*. Element 252 is of a piezoelectric ceramic composition that is polarized and configured with electrodes on opposing faces 252*a* and 252*b* to provide a primary direction of vibration along its thickness in response to an appropriate oscillatory electrical stimulus from circuitry 230.

Element 252 is oriented to place face 252*a* at an oblique angle relative to surface 262 of liquid L. Surface 262 corresponds to the generally planar surface formed when liquid L is still or at rest. Surface 262 extends along axis H, and correspondingly axis H is generally parallel to the plane of surface 262. As shown, liquid L is at a desired level selected in relation to focal point FP of element 252. Focal point FP is represented by cross-hairs at the intersection of focal axis 264 and surface 262. Focal axis 264 also intersects a midpoint of face 252*a*. Accordingly, the focal length of element 252 is represented by the line segment along axis 264 from face 252*a* to focal point FP. The orientation of element 252 results in formation of an acute angle A between axis H and focal axis 264. In one preferred form, acute angle A is less than about 85 degrees. In a more preferred form, acute angle A is less than about 60 degrees. In an even more preferred form, acute angle A is in a range of about 30 to about 35 degrees. It should be appreciated that for all these forms, a complementary obtuse angle is formed between axis H and focal axis 264, and such forms could additionally or alternatively be specified by obtuse angle values.

It has been found that the oblique angle orientation of a piezoelectric elements in this manner can enhance droplet and mist formation when activated by the appropriate electrical stimulus. In alternative embodiments, multiple like configured or differently configured elements can be included; where such differences can be in terms of size, shape, face curvature, composition, angular orientation, and the like. Alternatively or additionally, operating frequency, patterning of multiple elements, quantity of elements, and/or power level can vary. Also, operation with an operator or automated control station can be provided as previously described in connection with system 20. In one particular alternative, one or more obliquely angled elements 252 are combined with one or more elements 52 oriented as shown in system 20; where the focal axes FA are generally perpendicular to surface S and parallel to one another.

Figure 5:
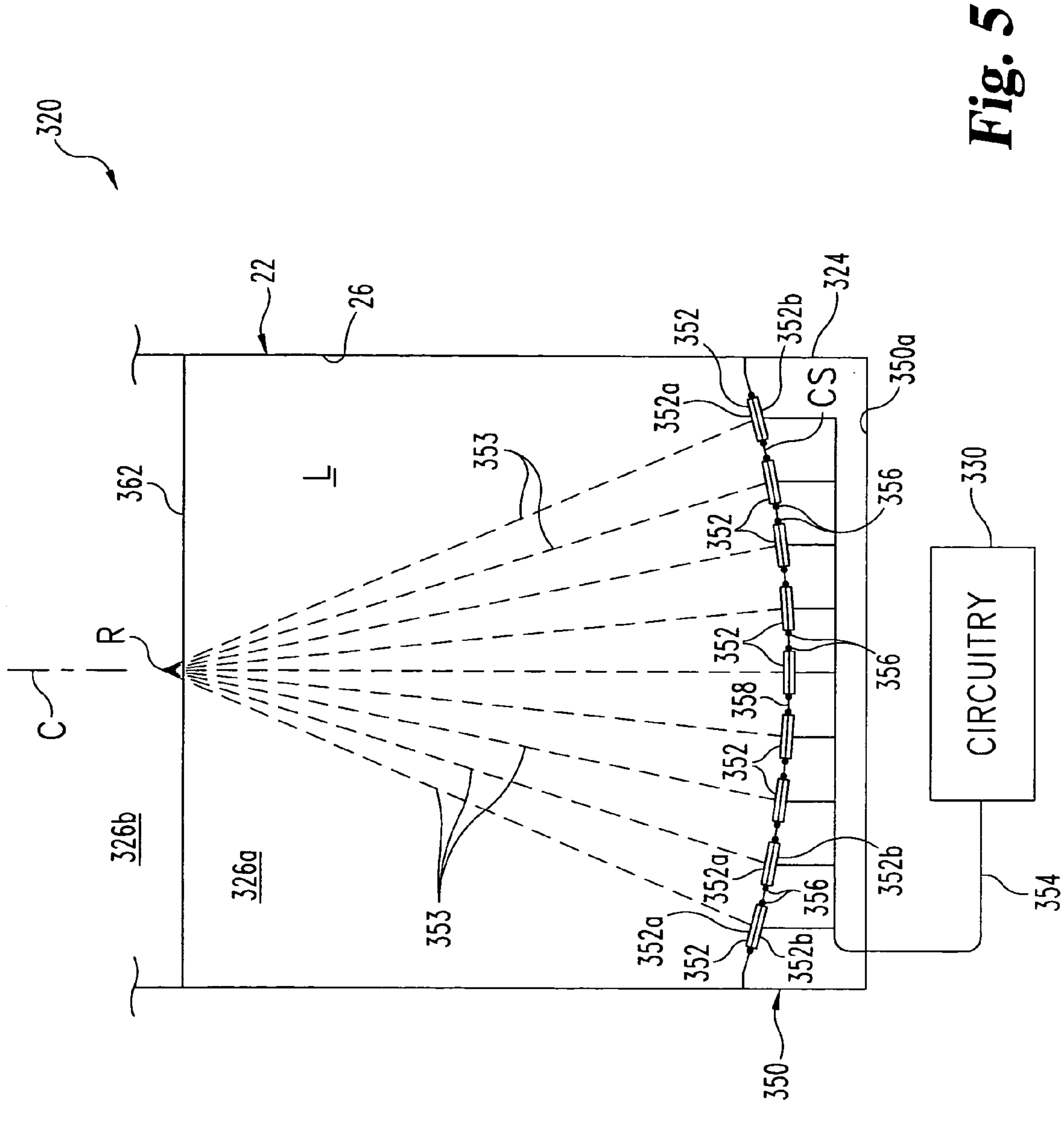
FIG. 5 is a partial, schematic view of a third droplet generation system.

FIG. 5 illustrates one arrangement of differently angled elements in the form of droplet generation system 320, where like reference numerals refer to like features of previously described embodiments. System 320 includes container 22 with base 324. Container 22 defines hollow interior chamber 26 holding liquid L in reservoir portion 326*a*. Head space 326*b* is provided above liquid L. Container 22 can be coupled to source 32 via valve 34, generator 36, and/or conduit 40 in the manner previously described in connection with FIG. 1 (not shown). Container 22 and base 324 are again schematically illustrated in section to show certain internal features.

Base 324 includes transducer assembly 350. Assembly 350 includes several piezoelectric elements 352. Elements 352 each include face 352*a* in contact with liquid L and opposing face 352*b* in contact with air in assembly space 350*a*. Each element 352 is mounted in relation to an aperture through floor member 358 with mounting seal 356 to prevent leakage of liquid L into space 350*a*. Elements 352 are electrically coupled to circuitry 330 by cabling 354 in a standard manner. Circuitry 330 includes one or more driver circuits for elements 352 of the circuit 130*a* type shown in FIG. 6, the circuit 130*b* type shown in FIG. 7, or such different type as would occur to those skilled in the art. Some or all of circuitry 330 can reside in space 350*a*. Elements 352 are each of a piezoelectric ceramic composition that is polarized and configured with electrodes on corresponding opposing faces 352*a* and 352*b* to provide a primary direction of vibration along its thickness in response to an appropriate oscillatory electrical stimulus from circuitry 330.

Elements 352 are arranged in a pattern corresponding to a curved surface contour CS that is concave in shape. Each element 352 more particularly is generally tangent to a point along contour CS such that they are at angular orientations that differ with the distance from surface 362 of liquid L, and are generally symmetric about a central axis C. Accordingly, elements 352 collectively define a discrete set of points along a concave surface. For focal axes 353 that are generally of the same length for each of elements 352, operation of assembly 350 can be similar to that of a single large concave element. As illustrated, elements 252 and container 22 can be structured to cause some or all of axes 353 to intersect in a desired region R within container 22. Region R can be determined relative to a desired level of liquid L in container 22. Only a few of elements 352, faces 352*a*, faces 352*b*, seals 356, and axes 353 are designated by reference numerals in FIG. 5 to preserve clarity. It should be understood that for the schematic sectional view of FIG. 5, CS is only illustrated with respect to the view plane. Additionally, elements 352 can be arranged to approximate a curved surface along a plane perpendicular to the FIG. 5 view plane. In one nonlimiting example, concentric rings of elements 352 about axis C are positioned at progressively lower levels as axis C is approached to approximate a concave bowl. In still other embodiments, elements 352 follow a curved path with respect to just a single plane of the type illustrated in FIG. 5 or are differently arranged along one or more curvilinear and/or rectilinear pathways.

It should be understood that focal axes 353 of several of elements 353 are oriented at oblique angles relative to surface 362 of liquid L. However, in this example, the center element 352 has axis 353 that is generally perpendicular to surface 362. Also, while member 358 is shown with a generally curved shape in correspondence to a concave surface section, in other embodiments, some or all of elements can be differently coupled to container 22. For example, one or more elements can be attached to a side wall of container 22. In another example, elements 352 can be coupled to pedestals of different heights corresponding to a concave surface. In other embodiments, differently shaped contours are followed/defined with elements 352.

In yet further embodiments, differently configured elements can be included in terms of size, shape, face curvature, and/or composition. Alternatively or additionally, operating frequency, quantity of elements, and/or power level can vary. Also, operation with an operator or automated control station can be provided as previously described in connection with system 20. In other alternatives, one or more elements 352 are combined with one or more elements 52 and/or 252. Indeed, systems 20, 220, and 320 can be combined in various manners relative to a target droplet generation application.

A further embodiment includes: a container to hold a liquid and a quantity of piezoelectric elements coupled to the container. The piezoelectric elements and the container are structured to cover the piezoelectric elements with the liquid when held in the container at an operable level. The piezoelectric elements are responsive to a corresponding oscillatory electrical stimulus to produce acoustic energy to form a mist from a portion of the liquid held in the container that includes droplets each having a diameter of one micrometer or less. Also included is circuitry coupled to the piezoelectric elements that is operable to provide the corresponding oscillatory electrical stimulus to each of the piezoelectric elements at a desired frequency. In one preferred form of this embodiment, the quantity of elements number 4 or more. In a more preferred form of this embodiment, the quantity of elements number 20 or more. In an even more preferred form of this embodiment, the quantity of elements number 100 or more.

Optionally, this embodiment further includes: a conduit in fluid communication with the container to direct at least a portion of the mist to a desired location; the piezoelectric elements being generally uniformly spaced apart from one another along a base of the container; at least one of the piezoelectric elements having a focal length at or above the operable level; at least one of the piezoelectric elements having a focal length along a focal axis that obliquely intersects an axis generally parallel to the liquid surface at rest to form an angle in a range of about 30 through 35 degrees; and/or the piezoelectric elements being arranged to correspond to a concave surface pattern.

Still another embodiment of the present invention comprises: providing a container coupled to several piezoelectric elements; determining a desired liquid level for the container as a function of one or more focal lengths of the piezoelectric elements; placing a liquid in the container to the desired liquid level to cover the piezoelectric elements; activating the piezoelectric elements with an oscillatory electrical stimulus to direct acoustic energy through the liquid; and converting the liquid to mist at a rate of at least 0.1 liter per minute in response to the acoustic energy from the piezoelectric elements. In a preferred embodiment, this rate is at least 0.25 liter per minute. In a more preferred embodiment, this rate is at least 1 liter per minute.

Yet a further embodiment comprises: a container operable to hold a liquid; several piezoelectric elements coupled to the container, and circuitry coupled to the piezoelectric elements. These elements each have a first face opposite a second face, and are each responsive to a corresponding electrical stimulus from the circuitry to produce acoustic energy with a respective focal length along a corresponding focal axis. The first face of each of the piezoelectric elements is positioned within the container to be covered by the liquid when the liquid is placed in the container to an operable level corresponding to the respective focal length of each of the piezoelectric elements. When the piezoelectric elements are activated by the corresponding electrical stimulus from the circuitry, the acoustic energy produced by the piezoelectric elements converts the liquid to mist at a rate of at least 0.1 liter per minute when the liquid is placed in the container to the operable level. In a preferred embodiment, this rate is at least 0.25 liter per minute. In a more preferred embodiment, this rate is at least 1 liter per minute.

EXPERIMENTAL EXAMPLES

The following are nonlimiting experimental examples of the present invention and are in no way intended to limit the scope of any aspect of the present invention.

First Experimental Example

A first experimental unit was made and tested for mist production from water. This unit had a 96 channels and 100 piezoelectric elements with separate oscillators and amplifiers (FIG. 6 driver circuit type). The transducer assembly contained 100 elements each 1 inch (") in diameter with a concave radius of 1.5" (collectively the "transducer"). The operating frequency of the elements was 2.5 MHz. The transducer elements were arranged in a square 10×10 array in a metal housing with the concave transducer surfaces in contact with water. The transducer housing was approximately 12" square. The optimum water depth for each element was approximately 1.4". Each element had an individual impedance matching circuit and a cable for connection to an oscillator/amplifier channel. The electronic circuitry was contained in a separate housing. There were 96 channels, each with a separate oscillator and power amplifier. Each oscillator had a variable frequency control to allow its frequency to be set to the optimum frequency for the transducer. The power level of all channels were controlled simultaneously by varying the voltage from the power supply to the amplifier circuit. The nominal operating power level was 25 W (Watts) per channel. Each element produced approximately 10 mL (milliliter) per minute of mist giving a combined output of approximately 1 liter/minute. The mean particle size of the mist produced was 2.3 μm.

Second Experimental Example

A second experimental unit was built and tested for mist production form water. This unit was designed to produce 250 mL/minute of mist of 3 μm mean particle size. This unit had 25 flat elements 0.51" diameter arranged in a 5×5 square array. The operating frequency was 1.6 MHz. The driver circuitry was of the second type (see FIG. 7) with a power oscillator for each element. The transducer elements and the oscillator circuitry were mounted in a circular housing of 8" diameter. A single cable connected the transducer/circuitry housing to the power supply. The power level was controlled by adjusting the voltage supplied to all the oscillators.

Other Experimental Examples

Experiments have been conducted with generally flat elements of the circular type, rectangular elements, and circular elements with concave spherical curvatures have been tried. Each of these element types had conductive electrodes on opposite faces. Multiple element experiments have been conducted with linear element arrays, rectangular element arrays, and circularly symmetric patterns.

All publications, patents, and patent applications cited in this specification are herein incorporated by reference as if each individual publication, patent, or patent application were specifically and individually indicated to be incorporated by reference and set forth in its entirety herein, including, but not limited to: Berger, Harvey L., "Ultrasonic Liquid Atomization: Theory and Application", Partridge Hill Publishers, Hyde Park, N.J., 1998. Any theory, mechanism of operation, proof, or finding stated herein is meant to further enhance understanding of the present invention and is not intended to make the present invention in any way dependent upon such theory, mechanism of operation, proof, or finding. While the invention has been illustrated and described in detail in the drawings and foregoing description, the same is to be considered as illustrative and not restrictive in character, it being understood that only the selected embodiments have been shown and described and that all changes, modifications, and equivalents that come within the spirit of the invention as defined herein or by the following claims are desired to be protected.

What is claimed is:

1. An apparatus, comprising:

a container operable to hold a liquid;

circuitry operable to provide an electrical stimulus;

a piezoelectric element electrically coupled to the circuitry, the piezoelectric element including a first face positioned beneath the liquid when the liquid is placed in the container, the piezoelectric element being responsive to the electrical stimulus to produce acoustic energy that causes droplets to form from the liquid; and a conduit in fluid communication with a head space of the container to direct the droplets to a desired location;

wherein the piezoelectric element has a focal length along a focal axis intersecting the first face, the piezoelectric element and the container being structured in relation to one another to form an acute angle between the focal axis and an axis generally parallel to a surface of the liquid when the liquid is at rest in the container, the acute angle being less than 85 degrees.

2. The apparatus of claim 1, wherein the circuitry is operable to provide the electric stimulus at a frequency of at least 8 megahertz.

3. The apparatus of claim 1, further comprising several other piezoelectric elements coupled to the container.

4. The apparatus of claim 3, wherein the piezoelectric element and the other piezoelectric elements are positioned relative to one another in an arrangement corresponding to a concave surface and each have a focal axis oriented to intersect one another within the container in accordance with the arrangement.

5. The apparatus of claim 3, wherein the piezoelectric element and the other piezoelectric elements number at least 20.

6. The apparatus of claim 1, wherein the acute angle is less than 60 degrees.

7. The apparatus of claim 1, wherein the acute angle is between about 30 and 35 degrees.

8. An apparatus, comprising:

a container operable to hold a liquid;

several piezoelectric elements coupled to the container, the piezoelectric elements each being responsive to a corresponding electrical stimulus to produce acoustic energy with a respective focal length along one of a corresponding number of focal axes, the piezoelectric elements being positioned relative to one another to cause at least some of the focal axes to intersect one another within the container and the piezoelectric elements being arranged to be covered by the liquid when the liquid is placed in the container to an operable level;

circuitry coupled to the piezoelectric elements, the circuitry being operable to provide the corresponding electrical stimulus to each of the piezoelectric elements; and a conduit in fluid communication with the container, the acoustic energy of each of the elements being directed through the liquid to form droplets when the liquid is placed in the container, the conduit being oriented to direct at least a portion of the droplets to a desired location.

9. The apparatus of claim 8, wherein the piezoelectric elements are spatially oriented in an arrangement corresponding to a concave surface.

10. The apparatus of claim 9, wherein the focal axes are approximately perpendicular to a tangent of the concave surface.

11. The apparatus of claim 8, wherein at least some of the focal axes form an angle oblique to a surface of the liquid when the liquid is at rest at the operable level.

12. The apparatus of claim 8, wherein the focal axes intersect at a predefined region determined relative to the operable level of the liquid.

13. The apparatus of claim 8, wherein the circuitry is operable to produce the corresponding electrical stimulus as a waveform with a frequency of at least 8 megahertz, and at least 20% of the droplets produced with the apparatus have a diameter of one micrometer or less.

14. A method, comprising:

providing a container coupled to a piezoelectric element;

placing a liquid in the container to a selected level to cover the piezoelectric element;

activating the piezoelectric element with an electrical stimulus to direct acoustic energy through the liquid along a focal axis, the focal axis forming an acute angle with an axis parallel to the selected level;

forming a mist from a portion of the liquid in response to the acoustic energy; and directing the mist to a desired location with a conduit in fluid communication with the container.

15. The method of claim 14, which includes arranging the piezoelectric element and several other piezoelectric elements in a pattern corresponding to a concave surface with corresponding focal axes that intersect in a region determined relative to a desired liquid level.

16. The method of claim 14, wherein at least 20% of the mist is comprised of droplets with a diameter of one micrometer or less.

17. The method of claim 14, wherein the mist has a mean droplet diameter of one micrometer or less.

18. The method of claim 14, wherein the electrical stimulus is provided at a frequency of at least 8 megahertz.

19. The method of claim 18, wherein the frequency is at least 10 megahertz.

20. A method, comprising:

providing a container coupled to at least 20 piezoelectric elements;

determining a desired liquid level for the container as a function of one or more focal lengths of the piezoelectric elements;

placing a liquid in the container to the desired liquid level to cover the piezoelectric elements;

activating the piezoelectric elements with an electrical stimulus provided at a frequency of at least eight megahertz to direct acoustic energy through the liquid; and forming a mist from a portion of the liquid in response to the acoustic energy, the mist including droplets with a diameter of 1 micron or less;

wherein the piezoelectric elements each include a second face opposite the first face, the second face is exposed to air while the first face of each of the piezoelectric elements is loaded by the liquid, the piezoelectric elements number at least 100 and are generally evenly spaced apart from one another along a base of the container, and the rate is at least 1 liter per minute.

21. The method of claim 20, which includes positioning one or more of the piezoelectric elements to form an oblique angle with an axis corresponding to an operable level of the liquid in the container.

22. The method of claim 20, which includes arranging the piezoelectric elements in a pattern corresponding to a concave surface with corresponding focal axes that intersect in a region determined relative to the desired liquid level.

23. The method of claim 20, wherein at least 20% of the mist is comprised of the droplets with the diameter of one micrometer or less.

24. The method of claim 20, wherein at least 50% of the mist is comprised of the droplets with the diameter of one micrometer or less.

25. The method of claim 20, wherein the frequency is at least 10 megahertz and the mist has a mean droplet diameter of one micrometer or less.

26. A method, comprising:

providing a container coupled to several piezoelectric elements;

determining a desired liquid level for the container as a function of one or more focal lengths of the piezoelectric elements;

placing a liquid in the container to the desired liquid level to cover the piezoelectric elements, the piezoelectric elements each including a first face mechanically loaded by the liquid after said placing;

activating the piezoelectric elements with an oscillatory electrical stimulus to direct acoustic energy through the liquid;

in response to the acoustic energy from the piezoelectric elements, converting the liquid to mist at a rate of at least 0.1 liter per minute;

directing the mist to a desired location with a conduit in fluid communication with the container.

27. The method of claim 26, wherein at least 20% of the mist is comprised of the droplets with the diameter of one micrometer or less.

28. The method of claim 26, which includes positioning one or more of the piezoelectric elements to form an oblique angle with an axis corresponding to an operable level of the liquid in the container.

29. The method of claim 26, which includes arranging the piezoelectric elements in a pattern corresponding to a concave surface with corresponding focal axes that intersect in a region determined relative to the desired liquid level.

30. The method of claim 26, wherein the frequency is at least 8 megahertz and the piezoelectric elements number at least 20.

31. The method of claim 26, wherein the rate is at least 0.25 liter per minute.

32. An apparatus, comprising:

a container operable to hold a liquid;

means for converting the liquid to mist at a rate of at least 0.1 liter per minute when the liquid is placed in the container at an operable level, said converting means including several piezoelectric elements coupled to a base of the container and circuitry coupled to the piezoelectric elements, the circuitry being operable to provide an electrical stimulus to each of the piezoelectric elements to produce acoustic energy; and a conduit in fluid communication with a head space of the container to direct the droplets to a desired location.

33. The apparatus of claim 32, wherein the piezoelectric elements number at least 4.

34. The apparatus of claim 32 wherein the piezoelectric elements number at least 20 and the rate is at least 0.25 liter per minute.

35. The apparatus of claim 32 wherein the piezoelectric elements number at least 100 and the rate is at least 1 liter per minute.

* * * * *